United States Patent
Ren et al.

(10) Patent No.: US 12,122,762 B2
(45) Date of Patent: Oct. 22, 2024

(54) CRYSTAL FORM A OF NHE3 INHIBITOR, PREPARATION METHOD THEREFOR AND APPLICATION THEREOF

(71) Applicant: SHENZHEN RENTAI PHARMATECH LTD., Guangdong (CN)

(72) Inventors: Guobin Ren, Guangdong (CN); Dongxu Yi, Guangdong (CN); Jiajun Huang, Guangdong (CN)

(73) Assignee: SHENZHEN RENTAI PHARMATECH LTD., Guangdong (CN)

( * ) Notice: Subject to any disclaimer, the term of this patent is extended or adjusted under 35 U.S.C. 154(b) by 686 days.

(21) Appl. No.: 17/472,927

(22) Filed: Sep. 13, 2021

(65) Prior Publication Data

US 2021/0403450 A1    Dec. 30, 2021

Related U.S. Application Data

(63) Continuation of application No. PCT/CN2019/078165, filed on Mar. 14, 2019.

(51) Int. Cl.
*C07D 401/12* (2006.01)

(52) U.S. Cl.
CPC ........ *C07D 401/12* (2013.01); *C07B 2200/13* (2013.01)

(58) Field of Classification Search
CPC .................... C07D 401/12; C07B 2200/13
See application file for complete search history.

(56) References Cited

U.S. PATENT DOCUMENTS

| | | |
|---|---|---|
| 2020/0268741 A1 | 8/2020 | Charmot et al. |
| 2021/0186953 A1 | 6/2021 | Carreras et al. |

FOREIGN PATENT DOCUMENTS

| | | | |
|---|---|---|---|
| CN | 102333759 A | 1/2012 | |
| CN | 105392483 A | 3/2016 | |
| CN | 103819403 B | 1/2017 | |
| CZ | 2017-732 | 11/2017 | |
| CZ | 2018607 | 11/2018 | |
| CZ | 2018-248 | 12/2018 | |
| IN | 201811033137 | 9/2018 | |
| IN | 201911021892 | 6/2019 | |
| WO | 2018129557 A1 | 7/2018 | |
| WO | WO-2019091503 A1 * | 5/2019 | ......... A61K 31/4725 |
| WO | 2020051014 A1 | 3/2020 | |

OTHER PUBLICATIONS

Nilsson et al., 15(4) Molecular Pharmaceutics 1476-1487 (2018) (Year: 2018).*
Chinese First Office Action, Chinese National Intellectual Property Administration, Chinese Patent Application 2019800031710, published Mar. 24, 2022, 10 pages.
"Elucidating an Amorphous Form Stabilization Mechanism for Tenapanor Hydorchloride: Crystal Structure Analysis Using X-ray Diffraction, NMR Crystallography, and Molecular Modeling", Sten O. NilssonLill et al., "MOL. Pharmaceuticals", vol. 15, pp. 1476-1487, Feb. 28, 2018.
"Predicting the Physical Stability of Amorphous Tenapanor Hydrochloride Using Local Molecular Structure Analysis, Relaxation Time Constants, and Molecular Modeling", Sanjeev Kothari et al., "MOL.Pharmaceutics", vol. 16, pp. 943-951, 2019-01-30.
International Searching Authority; Written Opinion of the International Searching Authority; Date: Dec. 19, 2019; pp. 1-6.
International Searching Authority; International Search Report; pp. 1-4.
Chinese National Intellectual Property Administration; Notification of Second Office Action for corresponding application No. 2019800031710; Date of Notification: Aug. 9, 2022; pp. 1-4.

* cited by examiner

*Primary Examiner* — Timothy R Rozof
(74) *Attorney, Agent, or Firm* — Taft Stettinius & Hollister LLP; Stephen F. Rost

(57) ABSTRACT

Provided is crystal form A of N,N'-(10,17-dioxo-3,6,21,24-tetraoxa-9,11,16, 18-tetrazohexahexane-1,26-di-yl)bis(4-(6, 8-dichloro-2-methyl-1,2,3,4-tetrahydroisoquinoline-4-yl) benzene sulfonamide. The crystal form has good light stability, high-temperature stability, and high-humidity stability.

20 Claims, 8 Drawing Sheets

CRYSTAL FORM A OF NHE3 INHIBITOR, PREPARATION METHOD THEREFOR AND APPLICATION THEREOF

CROSS-REFERENCE TO RELATED APPLICATION

This application is a continuation application of International Patent Application No. PCT/CN2019/078165 with an international filing date of Mar. 14, 2019, designating the United States, now pending. The contents of the aforementioned application are incorporated herein by reference.

TECHNICAL FIELD

The present application relates to the technical field of crystal form preparation, in particular to crystal form A of NHE 3 inhibitor, preparation method therefor and application thereof.

BACKGROUND

Salts and body fluid accumulation could contribute to the onset of many diseases including heart failure, chronic kidney disease, end-stage renal disease, liver disease, etc., and even cause death. Salts and body fluid accumulation is considered by academia as risk factors that causes hypertension. Therefore, there is an urgent need for a mechanism to reduce sodium retention and body fluid retention while not impair the body fluid/Na dynamic equilibrium in the kidney.

N,N'-(10,17-dioxo-3,6,21,24-tetraoxa-9,11,16,18-tetraazahexacosane-1,26-diyl) bis(4-(6,8-dichloro-2-methyl-1,2,3,4-tetrahydroisoquinoline-4-yl) benzene sulfonamide of formula (I), also known as Tenapanor, is a Sodium/Hydrogen Exchanger 3 (NHE 3) inhibitor developed by ARDELYX, INC. (US). It is a compound for treating disorders associated with fluid retention or salt overload and gastrointestinal tract disorders (Chinese Patent CN 103819403 B).

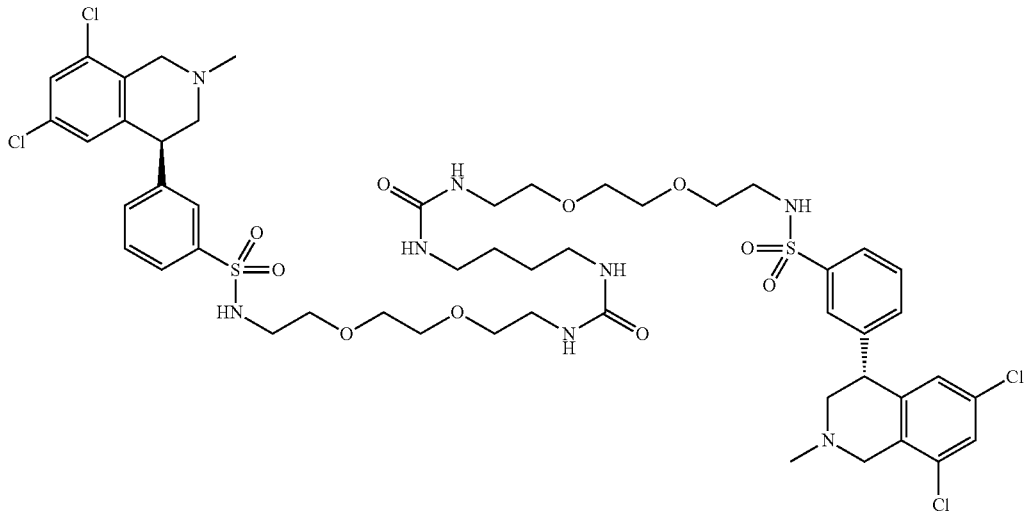

(I)

CN103819403B discloses a preparation method of the compound of formula (I). By referring to the following scheme, the preparation method comprises: adding compound 2 into compound 1 to perform acylation reaction to prepare the compound of formula (I). Then, the compound of formula (I) is separated and purified by High Performance Liquid Chromatography (HPLC).

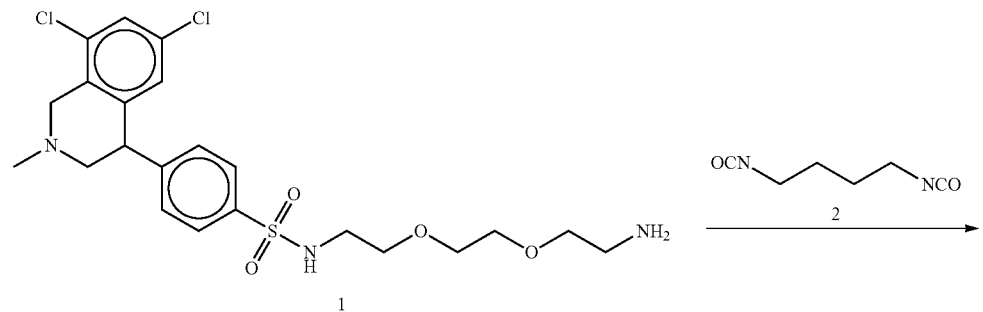

-continued

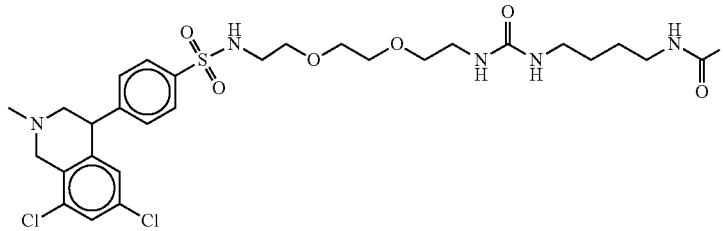

The inventors of the present invention prepared the compound of formula (I) according to the preparation method as described in CN103819403B, and carried out analysis. The results showed that the prepared compound had poor stability and high hygroscopicity. Especially, the prepared compound of formula (I) was found easy to decompose in environment of high temperature or high humidity or under strong lights, causing rapid decrease in the content of active ingredients. Because of hygroscopicity, the compound showed a weight increase up to 2% within 10 min under a humidity of RH 45%. Therefore, a strict management would be required during use of the compound of formula (I), rendering the compound unsuitable for use as a bulk pharmaceutical chemical.

SUMMARY

Accordingly, it is an object of the present application to provide a crystal form A of N, N'-(10,17-dioxo-3,6,21,24-tetraoxa-9,11,16,18-tetraazahexacosane-1,26-diyl) bis(4-(6,8-dichloro-2-methyl-1,2,3,4-tetrahydroisoquinoline-4-yl) benzene sulfonamide of formula (I), a preparation method therefor and application thereof. The crystal A has good stability and has a residual moisture content significantly reduced to below 0.4%.

In one aspect, the present application provides a crystal form A of N,N'-(10,17-dioxo-3,6,21,24-tetraoxa-9,11,16,18-tetraazahexacosane-1,26-diyl) bis(4-(6,8-dichloro-2-methyl-1,2,3,4-tetrahydroisoquinoline-4-yl) benzene sulfonamide of formula (I), wherein the X-ray powder diffraction (XRPD) thereof using Cu-Kα radiation has characteristic peaks at 2θ diffraction angles of 11.1±0.2°, 19.4±0.2°, 19.9±0.2° and 22.8±0.2°,

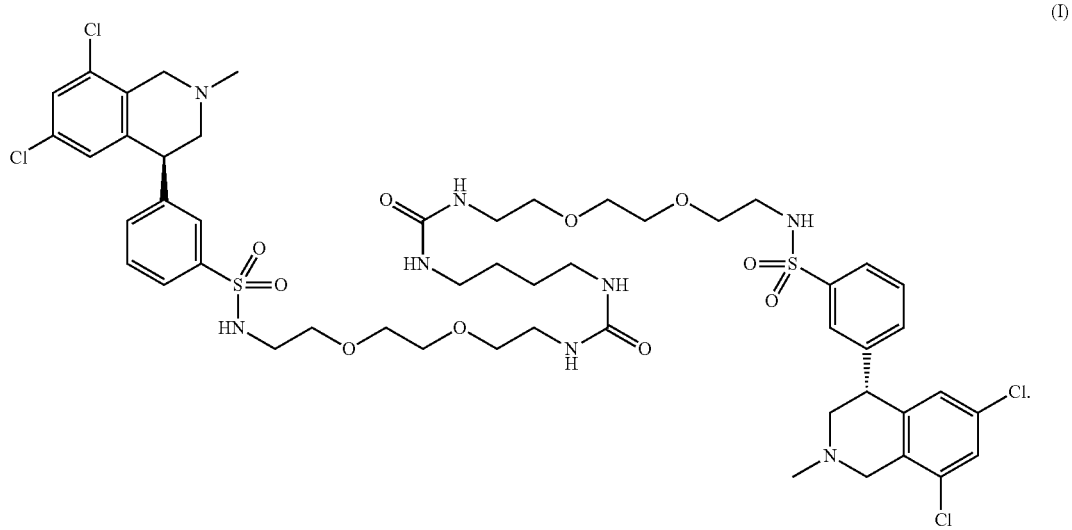 [SMILES: CN1Cc2c(Cl)cc(Cl)cc2[C@@H](c2cccc(S(=O)(=O)NCCOCCOCCNC(=O)NCCCCNC(=O)NCCOCCOCCNS(=O)(=O)c3cccc([C@@H]4CN(C)Cc5c(Cl)cc(Cl)cc54)c3)c2)C1]

(I)

In some embodiments, the X-ray powder diffraction of the crystal form A using Cu-Kα radiation has further characteristic peaks at 2θ diffraction angles of 8.6±0.2°, 13.2±0.2°, 13.5±0.2°, 22.1±0.2°, and 23.8±0.2°.

In some embodiments, the X-ray powder diffraction of the crystal form A using Cu-Kα radiation has further characteristic peaks at 2θ diffraction angles of 20.8±0.2°, 23.1±0.2°, 23.4±0.2°, 24.4±0.2°, and 24.9±0.2°.

In some embodiments, the X-ray powder diffraction of the crystal form A using Cu-Kα radiation has further characteristic peaks at 2θ diffraction angles of 5.9±0.2°, 6.1±0.2°, 11.8±0.2°, 15.0±0.2°, 15.5±0.2°, 16.0±0.2°, and 17.2±0.2°.

In some embodiments, the crystal form A has following characteristic peaks in X-ray powder diffraction pattern:

| No. of Peaks | 2θ (°) | Relative intensity (%) |
|---|---|---|
| 1 | 8.587 | 8.2 |
| 2 | 11.14 | 69.3 |
| 3 | 11.816 | 16.8 |
| 4 | 13.219 | 37.8 |
| 5 | 13.498 | 31.1 |
| 6 | 15.013 | 12.7 |
| 7 | 15.532 | 14.7 |
| 8 | 15.973 | 14.3 |
| 9 | 17.209 | 12.9 |
| 10 | 19.426 | 69.2 |
| 11 | 19.864 | 75.8 |
| 12 | 20.841 | 35.8 |
| 13 | 22.139 | 50.5 |
| 14 | 22.776 | 100 |
| 15 | 23.773 | 27.4 |

In some embodiments, the crystal form A has following characteristic peaks in X-ray powder diffraction pattern:

| No. of Peaks | 2θ (°) | Relative intensity (%) |
|---|---|---|
| 1 | 5.913 | 7.3 |
| 2 | 6.098 | 7.6 |
| 3 | 8.587 | 8.2 |
| 4 | 11.14 | 69.3 |
| 5 | 11.816 | 16.8 |
| 6 | 13.219 | 37.8 |
| 7 | 13.498 | 31.1 |
| 8 | 15.013 | 12.7 |
| 9 | 15.532 | 14.7 |
| 10 | 15.973 | 14.3 |
| 11 | 17.209 | 12.9 |
| 12 | 19.426 | 69.2 |
| 13 | 19.864 | 75.8 |
| 14 | 20.442 | 14.4 |
| 15 | 20.841 | 35.8 |
| 16 | 22.139 | 50.5 |
| 17 | 22.776 | 100 |
| 18 | 23.059 | 26 |
| 19 | 23.398 | 25.2 |
| 20 | 23.773 | 27.4 |
| 21 | 24.395 | 30.3 |
| 22 | 24.934 | 26.4 |

In some embodiments, the crystal form A has an X-ray powder refraction pattern substantially as shown in FIG. 2.

In some embodiments, the crystal form A has a characteristic absorption peak in a temperature range of 140° C.-150° C. measured by differential scanning calorimetry (DSC).

In some embodiments, the crystal form A has a differential scanning calorimetry curve substantially as shown in FIG. 3.

In some embodiments, the crystal form A has a weight loss of 0.4% before a temperature of 100° C. in its thermo gravimetric analysis (TGA) curve.

In some embodiments, the crystal form A has a thermo gravimetric analysis curve substantially as shown in FIG. 4.

In another aspect, the present application also provides a method for preparing the crystal form A, comprising the following steps of:
dissolving amorphous N,N'-(10,17-dioxo-3,6,21,24-tetraoxa-9,11,16,18-tetraazahexacosane-1,26-di-yl)bis(4-(6,8-dichloro-2-methyl-1,2,3,4-tetrahydroisoquinoline-4-yl)benzene sulfonamide by adding a good solvent thereto, performing a first cooling to room temperature, and adding a poor solvent thereto, and performing a second cooling, followed by standing, separating out solids and drying to obtain the crystal form A.

In some embodiments, the second cooling is performed at a rate of 18-24° C./min, preferably at a rate of 20° C./min.

In some embodiments, the good solvent is an organic solvent selected from the group consisting of a lower alcohol, a lower ketone and a lower nitrile; and wherein the poor solvent is methyl tert-butyl ether.

In some embodiments, the lower alcohol is selected from the group consisting of methanol, ethanol, isopropanol or n-butanol, and the lower ketone is acetone; and the lower nitrile is acetonitrile.

In some embodiments, a volume ratio of the good solvent to the poor solvent is 1:(8-14).

In another aspect, the present application further provides a pharmaceutical composition, comprising the above crystal form A and a pharmaceutically acceptable excipient.

In another aspect, the present application further provides use of a pharmaceutically effective amount of the crystal form A, or of the crystal form A prepared by the method of the present invention, or of the pharmaceutical composition, in the manufacture of a medicament for inhibiting NHE-mediated antiport of sodium ions and hydrogen ions in mammals.

In another aspect, the present application further provides use of a pharmaceutically effective amount of the crystal form A, or of the crystal form A prepared by the method of the present invention, or of the pharmaceutical composition, in the manufacture of a medicament for treating a disease associated with fluid retention or salt overload in mammals.

In another aspect, the present application further provides use of a pharmaceutically effective amount of the crystal form A, or of the crystal form A prepared by the method of the present invention, or of the pharmaceutical composition, in the manufacture of a medicament for treating a disease selected from the group consisting of heart failure, chronic kidney disease, end-stage renal disease, liver disease, and peroxisome proliferator-activated receptor gamma agonist-induced fluid retention, wherein the heart failure is preferably congestive heart failure.

In another aspect, the present application further provides use of a pharmaceutically effective amount of the crystal form A, or of the crystal form A prepared by the method of the present invention, or of the pharmaceutical composition, in the manufacture of a medicament for treating hypertension, edema and gastrointestinal tract disorder in mammals, wherein the hypertension is preferably associated with dietary salt intake; the edema is preferably induced by chemotherapy, premenstrual fluid overload or preeclampsia; and the gastrointestinal tract disorders are preferably gastrointestinal motility disorder, irritable bowel syndrome, chronic constipation, functional gastrointestinal tract disorders or Crohn's disease, wherein the chronic constipation is more preferably chronic idiopathic constipation, chronic constipation in patients with cystic fibrosis, or opioid-induced constipation, or calcium-supplement-induced constipation.

In some embodiments, the medicament is administered orally or by rectal suppository.

In another aspect, the present application further provides a method for treating a disease associated with fluid retention or salt overload in mammals, comprising the step of administering a pharmaceutically effective amount of the pharmaceutical composition to a patient.

The technical solutions of the present application have the following advantages:
1. The crystal form A of the compound of formula (I) provided in the present application has high purity, and good solubility in water, buffer solution or organic solvent, which is beneficial to prepare a medicament.
2. The crystal form A of the compound of formula (I) provided in the present application has good light stability, high temperature stability, accelerated stability and high humidity stability, and has a moisture content or other solvent content as low as 0.4%. When the relative humidity is increased from 0 to RH 90%, the crystal form A show a weight increase by hygroscopicity of not higher than 1%, indicating the moisture absorption by the crystal form A is slow. The crystal form A can be prepared with a simple preparation process under mild conditions, and the quality is stable, all of which facilitate large-scale industrial production.
3. The crystal form A of the compound of formula (I) provided by the present application has an improved powder flowability when compared with amorphous compound, and is possible to prepare formulations with stable active ingredient content.
4. The crystal form A of the compound of formula (I) provided by the present application has better efficacy in animal body, longer half-life period and higher exposure when compared with amorphous compound.

BRIEF DESCRIPTION OF THE DRAWINGS

In order to more clearly describe the specific embodiments of the present application or the technical solutions in the prior art, drawings used in the specific embodiments or the description of the prior art will be briefly introduced as follows. Obviously, the drawings in the following description are some embodiments of the present application, and other drawings can be obtained according to these drawings without paying creative labor for those skilled in the art.

DETAILED DESCRIPTION

The term "bulk pharmaceutical chemical" used in the following embodiments of the present application refers to N,N'-(10,17-dioxo-3,6,21,24-tetraoxa-9,11,16,18-tetraazahexacosane-1,26-diyl) bis(4-(6,8-dichloro-2-methyl-1,2,3,4-tetrahydroisoquinoline-4-yl) benzene sulfonamide, with a chemical purity of greater than 98%, provided by Shanghai Haoyuan Biomedical Technology Co., Ltd. Following experimental equipment and test conditions are used in the present application:
X-Ray Powder Diffractometer XRPD
  Model: BRUKER D8 DISCOVER (BRUKER, Germany)
  Method: Cu target Ka, voltage: 40 KV, current: 40 mA, test angle: 3-45°, scanning step: 0.02, exposure time: 0.2 S, slit width of light pipe: 1 mm, slit width of detector: 2.7 mm.
X-Ray Single Crystal Diffractometer SXRD
  Model: BRUKER D8 QUEST (BRUKER, Germany)
  Method: Cu target, voltage: 40 KV, current: 30 mA
Differential Scanning Calorimeter DSC
  Model: TA 250 (TA Instruments, US)
  Method: heating at a rate of 10° C./min.
Thermal Gravimetric Analysis TGA
  Model: TA 550 (TA Instruments, US);
  Method: heating at a rate of 10° C./min.
Dynamic Vapor Sorption DVS
  Model: DVS intrinsic (SMS, British);
  Method: 25° C., relative humidity is stepped up at a rate of 10% per step, and the judgment standard is change in moisture content is <0.002% over a 10-minute period.
Light Incubator
  Model: MGC-100 (Shanghai Yiheng Scientific Instrument Co., Ltd.)
Ultrasound Equipment
  Model: KQ-3200 (Shanghai Alloy Ultrasonic Equipment Co., Ltd.)
Programmable Temperature and Humidity Chamber for Drug Stability
  Model: CMA-100C (Shanghai Puhan Precision Equipment Co., Ltd.)

Embodiment 1 XRPD Analysis of Bulk Pharmaceutical Chemical

Figure 1:
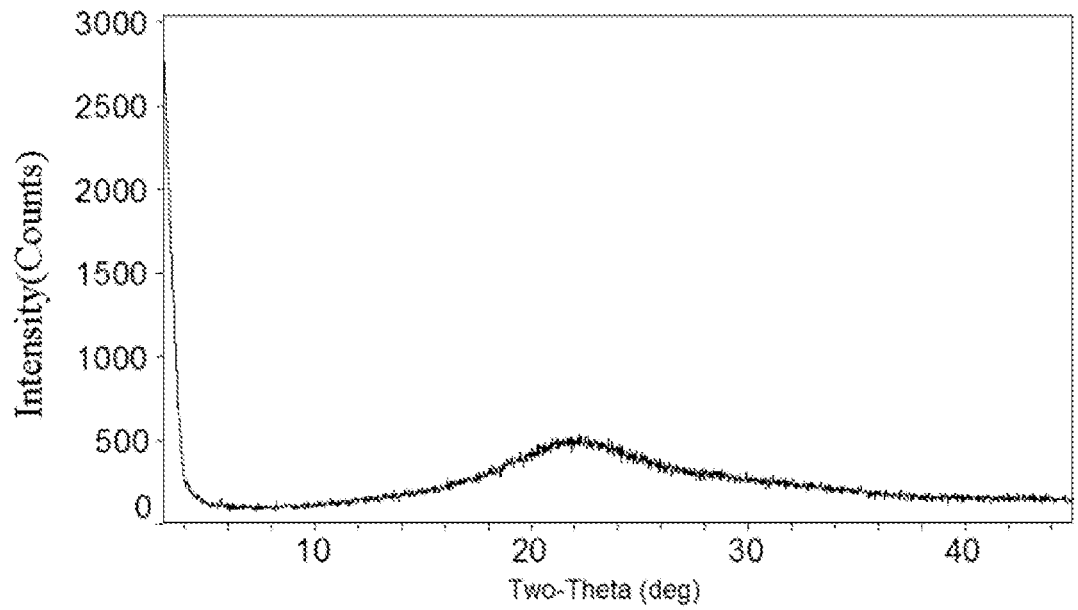
FIG. 1 shows an X-ray powder diffraction (XRPD) pattern of amorphous compound in embodiment 1 of the present application.

N,N'-(10,17-dioxo-3,6,21,24-tetraoxa-9,11,16,18-tetraazahexacosane-1,26-diyl) bis(4-(6,8-dichloro-2-methyl-1,2,3,4-tetrahydroisoquinoline-4-yl) benzene sulfonamide, with a chemical purity of greater than 98%, purchased from Shanghai Haoyuan Biomedical Technology Co., Ltd., is used as bulk pharmaceutical chemical. XRPD pattern for the bulk pharmaceutical chemical is measured and shown in FIG. 1. There are no characteristic peaks reflecting diffraction angles, interplanar spacing and relative intensity in the XRPD pattern, confirming that the bulk pharmaceutical chemical is amorphous.

Figure 2:
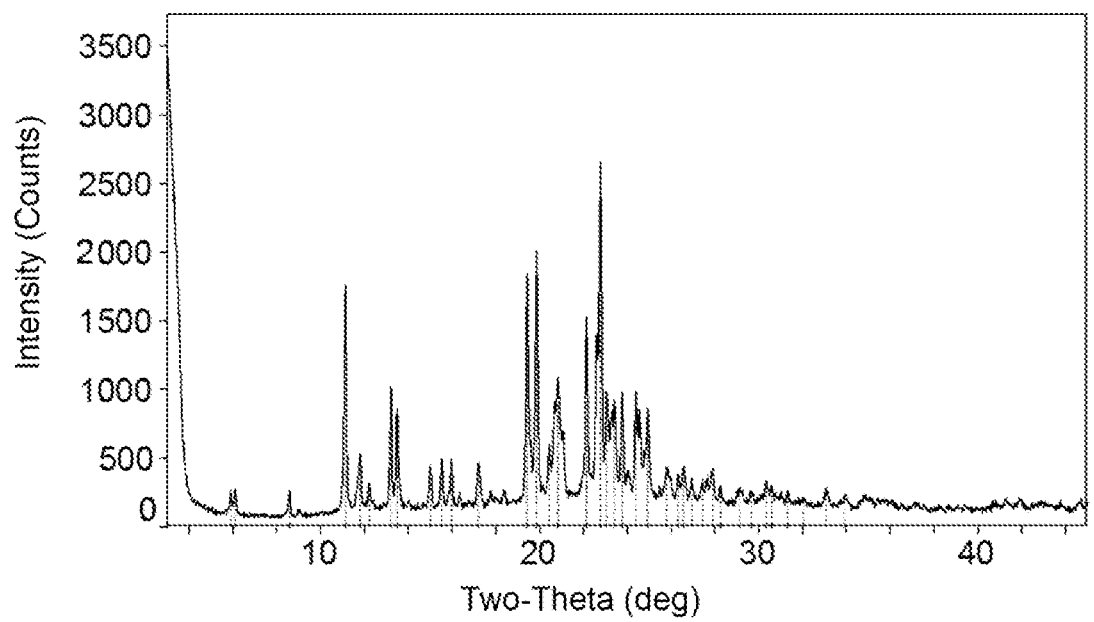
FIG. 2 shows an XRPD pattern (peak positions are marked) of crystal form A in embodiment 2 of the present application.

Embodiment 2 Preparation of Crystal Form A 30 mg of the bulk pharmaceutical chemical is weighed out, and 0.5 mL of methanol is added and heated to 50° C.

for dissolving. The resulting solution is cooled to room temperature, and 5 mL of methyl tert-butyl ether is added. The resulting solution is, then rapidly cooled to 4° C. at a rate of 20° C./min, followed by standing for 24 h at 4° C. Solid is separated from liquid and placed into a vacuum dryer, thus obtaining a crystal form A as an off-white powder. The XRPD pattern of crystal form A is shown in FIG. 2.

TABLE 1

Characteristic peaks of crystal form A

| 2-Theta | d (A) | I % |
|---|---|---|
| 5.913 | 14.96 | 7.3 |
| 6.098 | 14.48 | 7.6 |
| 8.587 | 10.29 | 8.2 |
| 11.14 | 7.94 | 69.3 |
| 11.816 | 7.48 | 16.8 |
| 12.22 | 7.24 | 7.3 |
| 13.219 | 6.69 | 37.8 |
| 13.498 | 6.55 | 31.1 |
| 15.013 | 5.90 | 12.7 |
| 15.532 | 5.70 | 14.7 |
| 15.973 | 5.54 | 14.3 |
| 17.209 | 5.15 | 12.9 |
| 19.426 | 4.57 | 69.2 |
| 19.864 | 4.47 | 75.8 |
| 20.442 | 4.34 | 14.4 |
| 20.841 | 4.26 | 35.8 |
| 22.139 | 4.01 | 50.5 |
| 22.776 | 3.90 | 100 |
| 23.059 | 3.85 | 26 |
| 23.398 | 3.80 | 25.2 |
| 23.773 | 3.74 | 27.4 |
| 24.395 | 3.65 | 30.3 |
| 24.934 | 3.57 | 26.4 |
| 25.793 | 3.45 | 9 |
| 26.328 | 3.38 | 6.7 |
| 26.569 | 3.35 | 9.5 |
| 26.93 | 3.31 | 6.3 |
| 27.442 | 3.25 | 6.1 |
| 27.904 | 3.19 | 9.9 |
| 28.246 | 3.16 | 4.6 |
| 29.125 | 3.06 | 4.9 |
| 29.658 | 3.01 | 3.6 |
| 30.34 | 2.94 | 6.4 |
| 30.597 | 2.92 | 4.9 |
| 31.305 | 2.86 | 3.7 |
| 32.039 | 2.79 | 2.3 |
| 33.073 | 2.71 | 5.7 |
| 33.933 | 2.64 | 3.8 |

Figure 3:
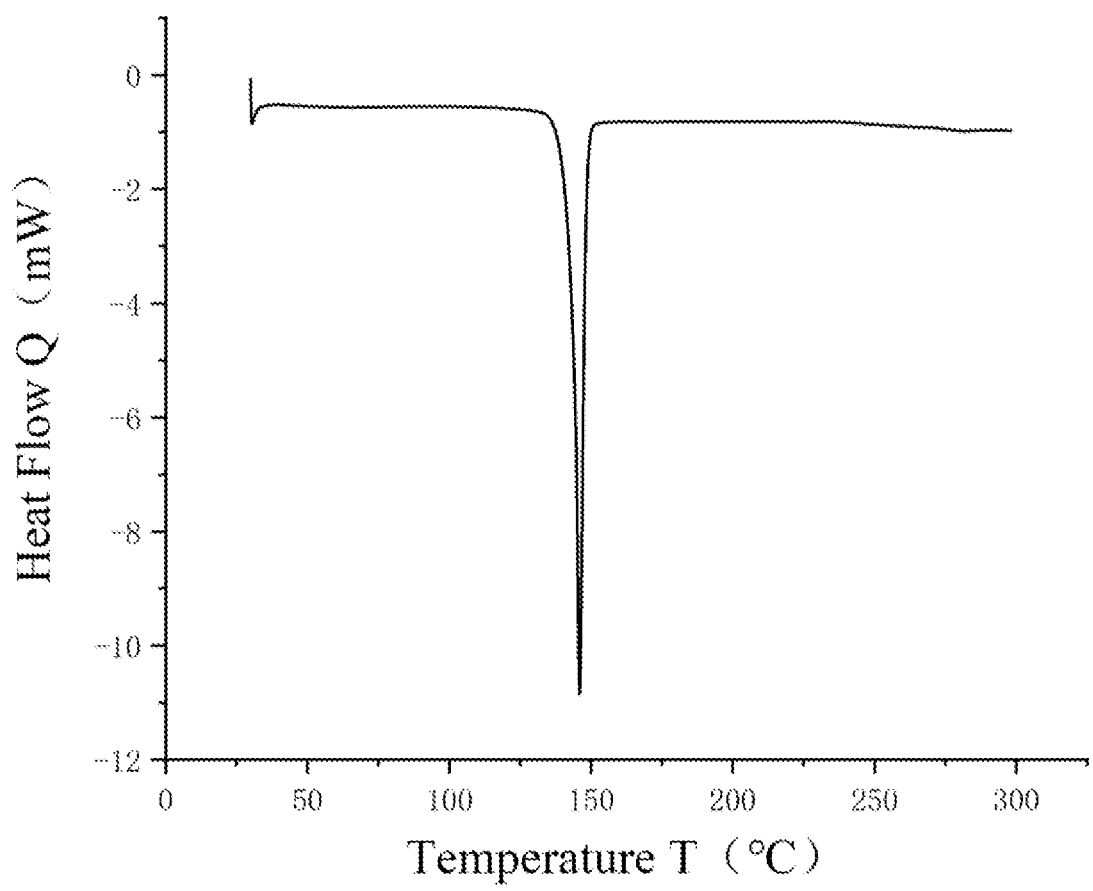
FIG. 3 shows a differential scanning calorimetry (DSC) curve of crystal form A in embodiment 2 of the present application.
Figure 4:
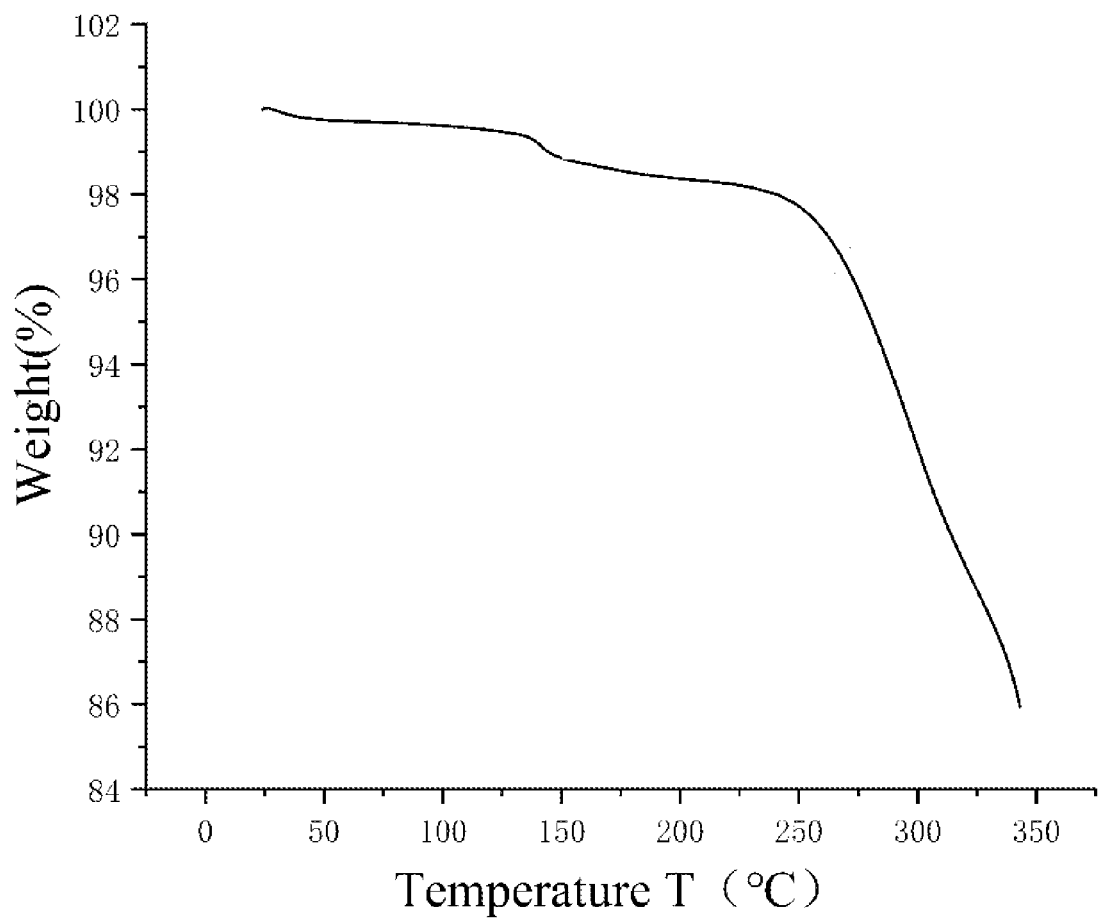
FIG. 4 shows a thermo gravimetric analysis (TGA) curve of crystal form A in embodiment 2 of the present application.

DSC and TGA curves for the crystal form A are measured and shown in FIGS. 3 and 4. It is observed that, there is one absorption peak at 145.9° C. in the DSC curve, and a weight loss of 0.4% before 100° C. in the TGA curve. This weight loss indicates that the sample contains a very small amount of volatile substances (less than 0.4%), and indicates the crystal form A is not a hydrate or other solvates, and also indicates that the obtained crystal form A has been fully dried.

Figure 5:
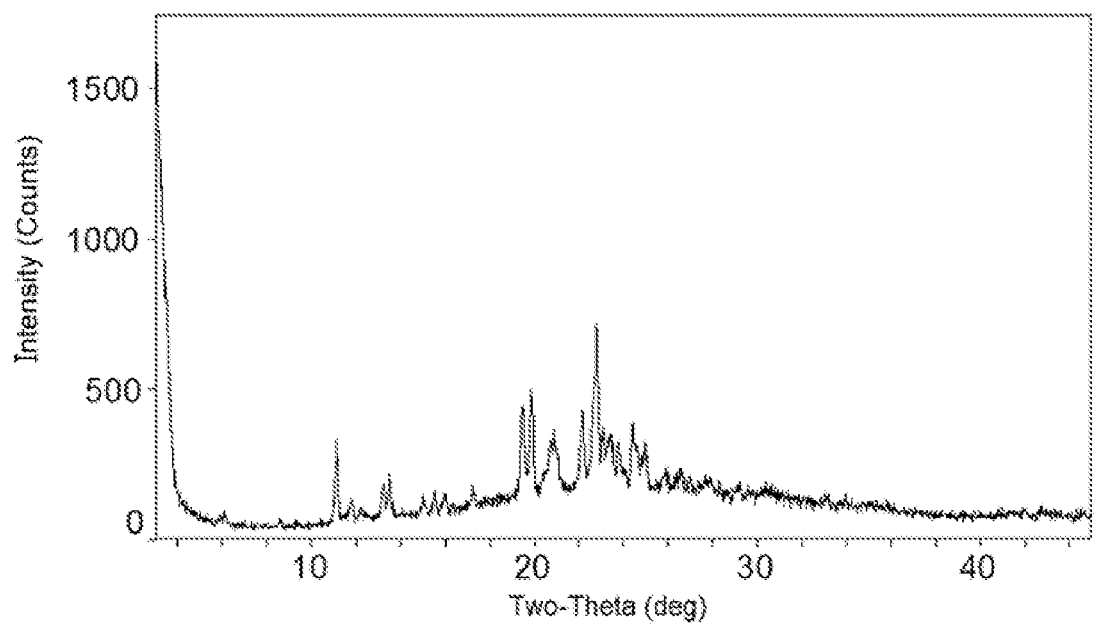
FIG. 5 shows an XRPD pattern of crystal form A in embodiment 3 of the present application.

Embodiment 3 Preparation of Crystal Form A 20 mg of the bulk pharmaceutical chemical is weighed out, and 0.5 mL of ethanol is added and heated to 50° C. for dissolving. The resulting solution is cooled to room temperature, and 5 mL of methyl tert-butyl ether is added. The resulting solution is then rapidly cooled to 4° C. at a rate of 20° C./min, followed by standing for 24 h at 4° C. Solid is separated from liquid and placed into a vacuum dryer, thus obtaining a crystal form A as an off-white powder. The XRPD pattern of crystal form A is shown in FIG. 5 which is substantially consistent with FIG. 2 of embodiment 2.

Figure 6:
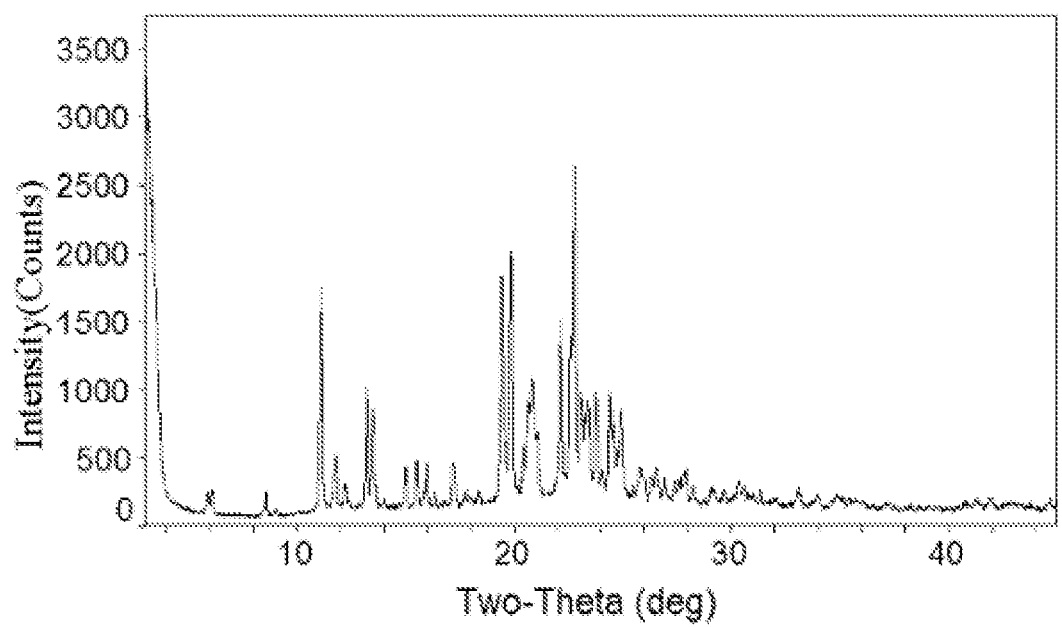
FIG. 6 shows an XRPD pattern of crystal form A in embodiment 4 of the present application.

Embodiment 4 Preparation of Crystal Form A 50 mg of the bulk pharmaceutical chemical is weighed out, and 0.3 mL of tetrahydrofuran is added and heated to 50° C. for dissolving. The resulting solution is cooled to room temperature, and 5 mL of methyl tert-butyl ether is added. The resulting solution is then rapidly cooled to 4° C. at a rate of 20° C./min, followed by standing for 24 h at 4° C. Solid is separated from liquid and placed into a vacuum dryer, thus obtaining a crystal form A as an off-white powder. The XRPD pattern of crystal form A is shown in FIG. 6 which is substantially consistent with FIG. 2 of embodiment 2.

Figure 7:
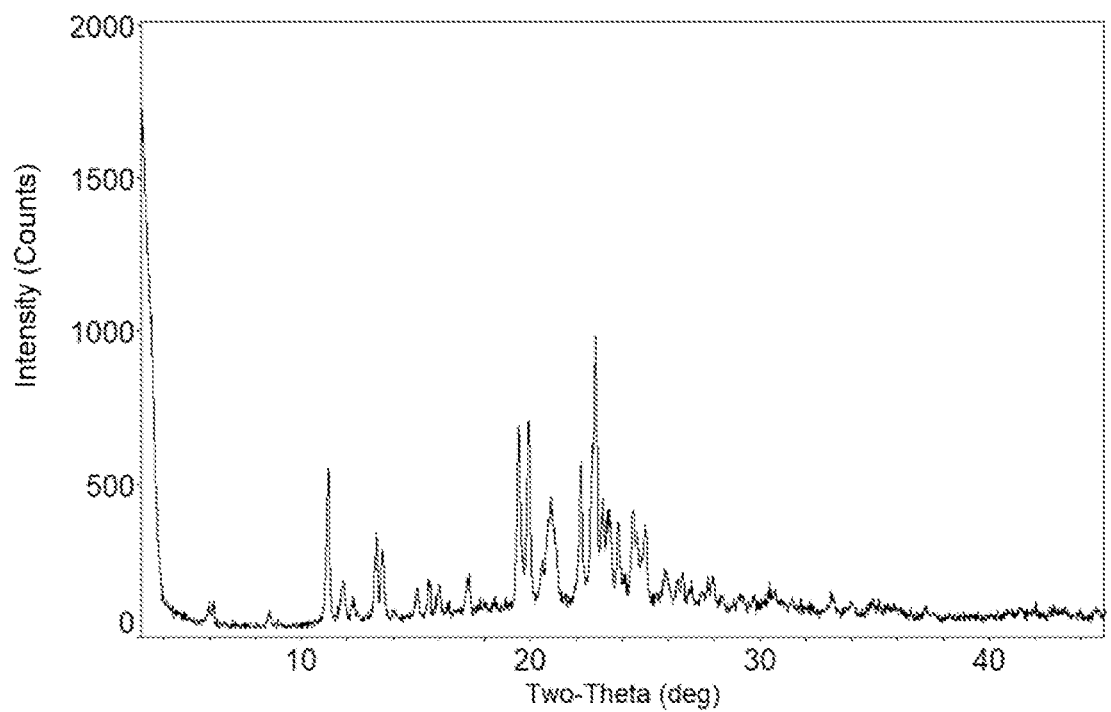
FIG. 7 shows an XRPD pattern of crystal form A in embodiment 5 of the present application.

Embodiment 5 Preparation of Crystal Form A 30 mg of the bulk pharmaceutical chemical is weighed out, and 0.5 mL of methanol is added and heated to 50° C. for dissolving. The resulting solution is cooled to room temperature, and 4 mL of methyl tert-butyl ether is added. The resulting solution is then rapidly cooled to 4° C. at a rate of 24° C./min, followed by standing for 24 h at 4° C. Solid is separated from liquid and placed into a vacuum dryer, thus obtaining a crystal form A as an off-white powder. The XRPD pattern of crystal form A is shown in FIG. 7 which is substantially consistent with FIG. 2 of embodiment 2.

Figure 8:
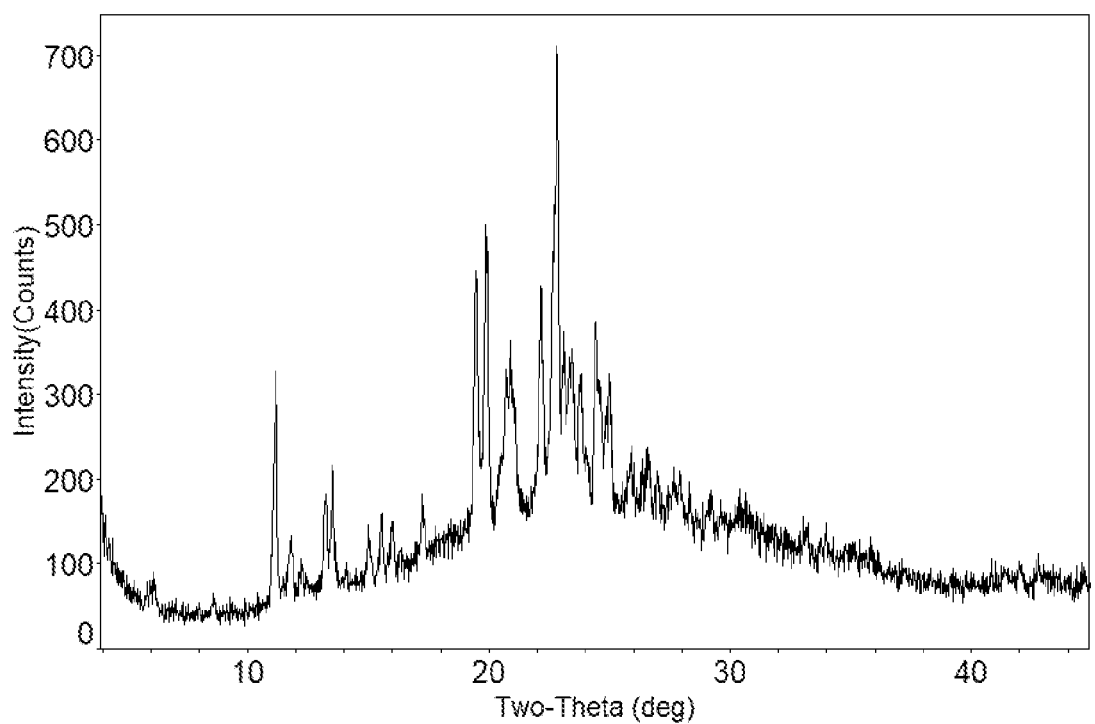
FIG. 8 shows an XRPD pattern of crystal form A in embodiment 6 of the present application.

Embodiment 6 Preparation of Crystal Form A 30 mg of bulk pharmaceutical chemical is weighed out, and 0.5 mL of methanol is added and heated to 50° C. for dissolving. The resulting solution is cooled to room temperature, and 7 mL of methyl tert-butyl ether is added. The resulting solution is then rapidly cooled to 4° C. at a rate of 18° C./min, followed by standing for 24 h at 4° C. Solid is separated from liquid and placed into a vacuum dryer, thus obtaining a crystal form A as an off-white powder. The XRPD pattern of crystal form A is shown in FIG. 8 which is substantially consistent with FIG. 2 of embodiment 2.

Experimental Example 1 Purity Study

Purities of the amorphous compound of embodiment 1 and the crystal forms A prepared in embodiments 2-6 are determined by HPLC. The results are as shown in table 2.

TABLE 2

Purities of crystal forms A and amorphous bulk pharmaceutical chemical

| Embodiments | Purity/% |
|---|---|
| Embodiment 1 | 98.83 |
| Embodiment 2 | 98.44 |
| Embodiment 3 | 98.33 |
| Embodiment 4 | 99.21 |
| Embodiment 5 | 98.58 |
| Embodiment 6 | 98.14 |

Experimental Example 2 Hygroscopicity Study

Dynamic vapor sorption (DVS) experiment are performed for the amorphous compound of embodiment 1 and the crystal form A prepared in embodiment 2 to obtain DVS curves under the following conditions: the temperature is 25° C., the relative humidity (RH) is stepped up from RH 0 to RH 90% at a rate of RH 10% per step, with 10 min for each step to reach equilibrium.

Figure 9:
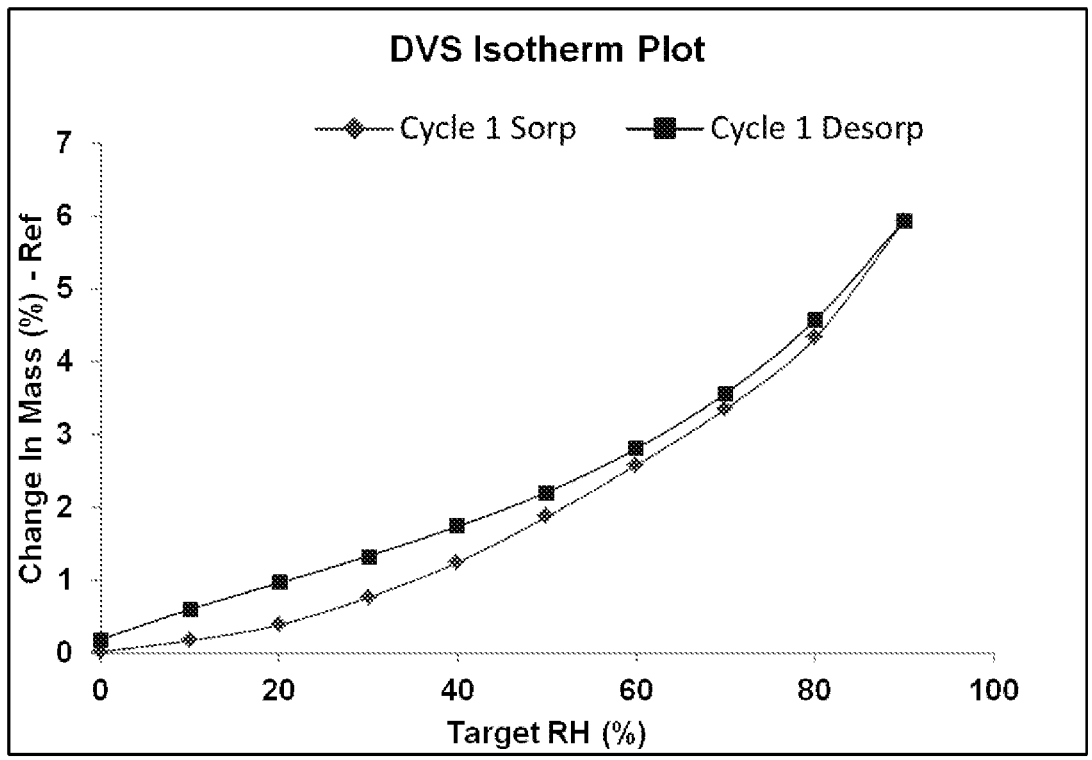
FIG. 9 shows a dynamic vapor sorption (DVS) curve measured in experimental example 2 for the amorphous compound in embodiment 1 of the present application.
Figure 10:
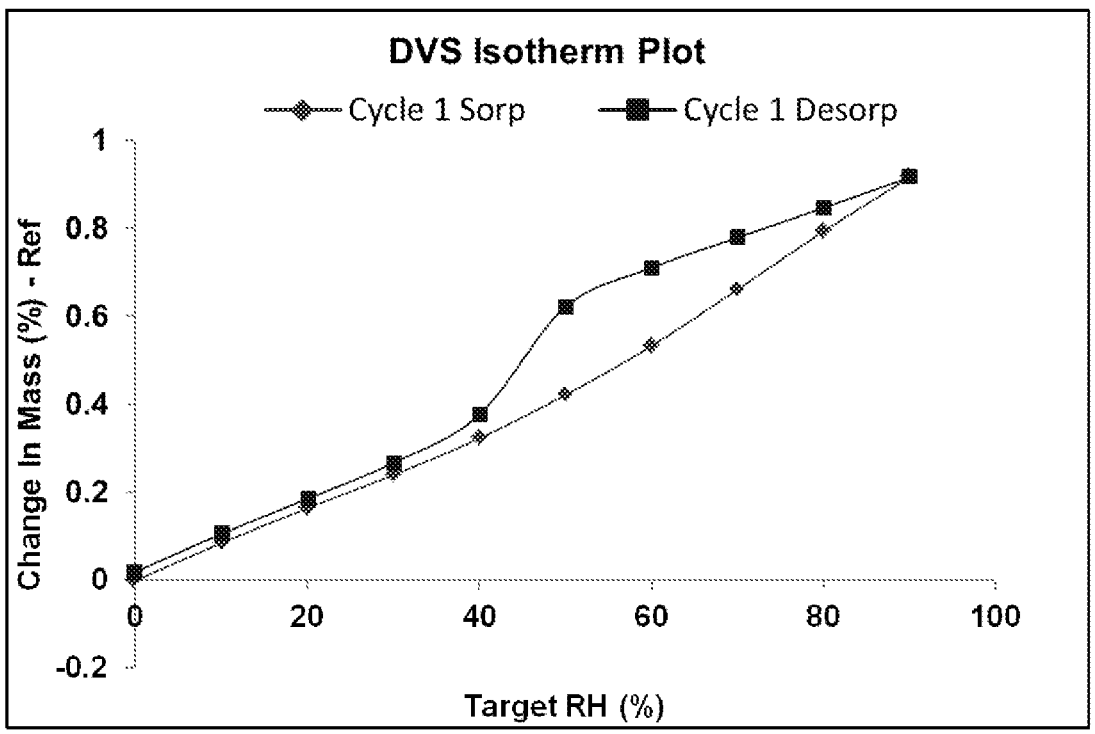
FIG. 10 shows a DVS curve measured in experimental example 2 for the crystal form A prepared in embodiment 2 of the present application.
Figure 11:
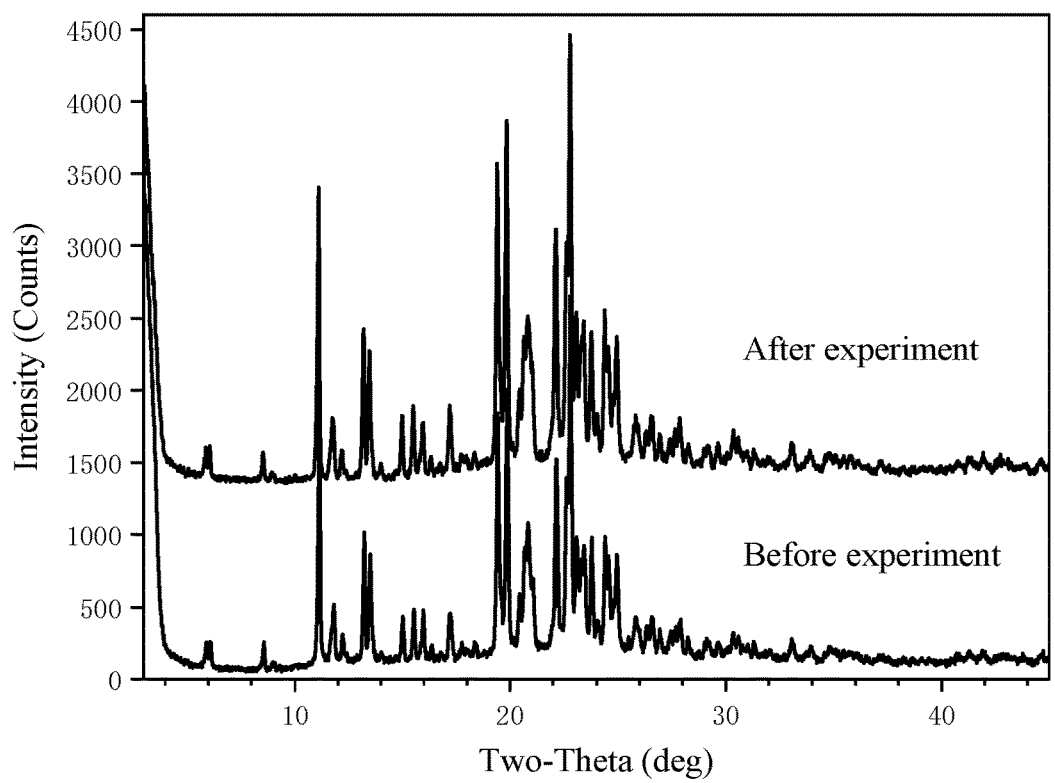
FIG. 11 shows comparison of XRPD patterns before and after DVS detection of the crystal form A prepared in embodiment 2 of the present application.

When RH 90% is completed, the amorphous compound has a weight increase of 7% due to moisture absorption (see FIG. 9). In contrast, the crystal form A has a weight increase of no more than 1%, and in each step of 10 min, the crystal form A has a weight change of less than 0.02% (see FIGS. 10 and 11), indicating that the crystal form A has a significantly reduced hygroscopicity, which is more conducive to transportation and storage of drugs.

Experimental Example 3 Stability Study

Figure 12:
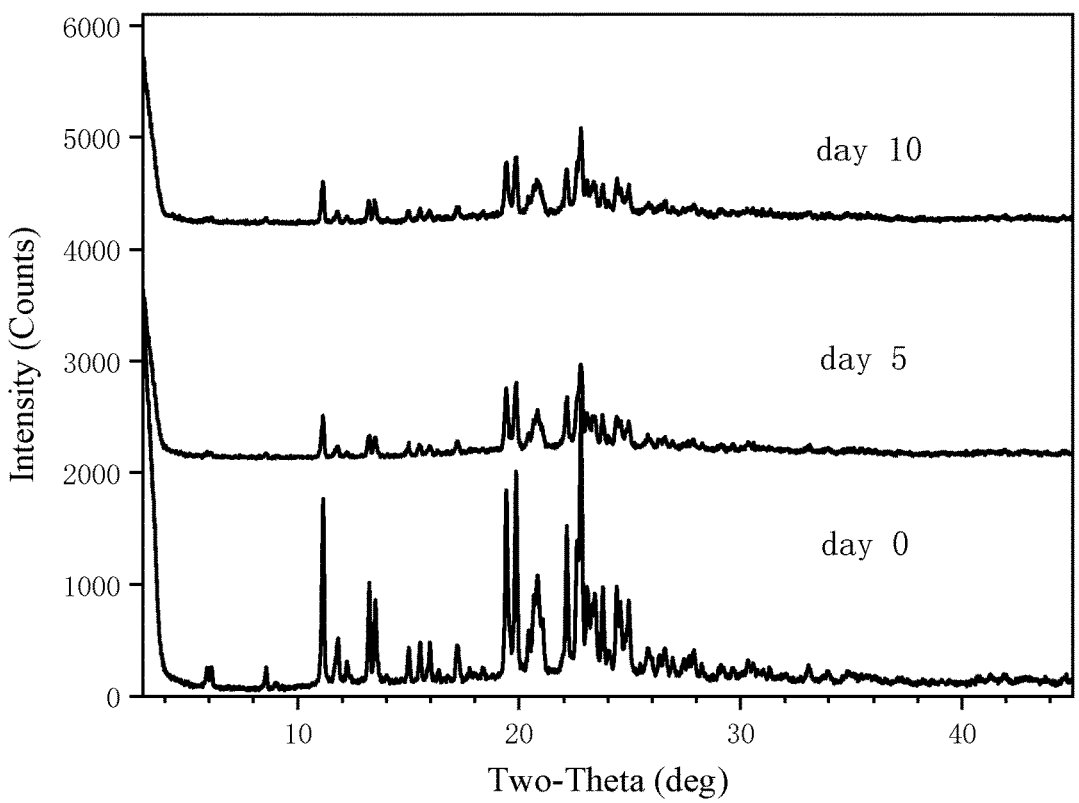
FIG. 12 shows comparison of XRPD patterns of crystal form A of the present application to study stability under lights.

Follow tests are performed for the amorphous bulk pharmaceutical chemical of embodiment 1 and the crystal form A prepared in embodiment 2:

(1) Light stability: the test sample is placed in an environment having a temperature of 25° C. and a light condition of 4500 Lux for 5 days and 10 days, respectively, to test the stability of the crystal form. Samples are collected at the same point at $5^{th}$ and $10^{th}$ day to measure content by HPLC peak area normalization method. The results are shown in table 3 and FIG. 12, indicating that the crystal form A has significantly improved light stability as compared to amorphous bulk pharmaceutical chemical.

Figure 13:
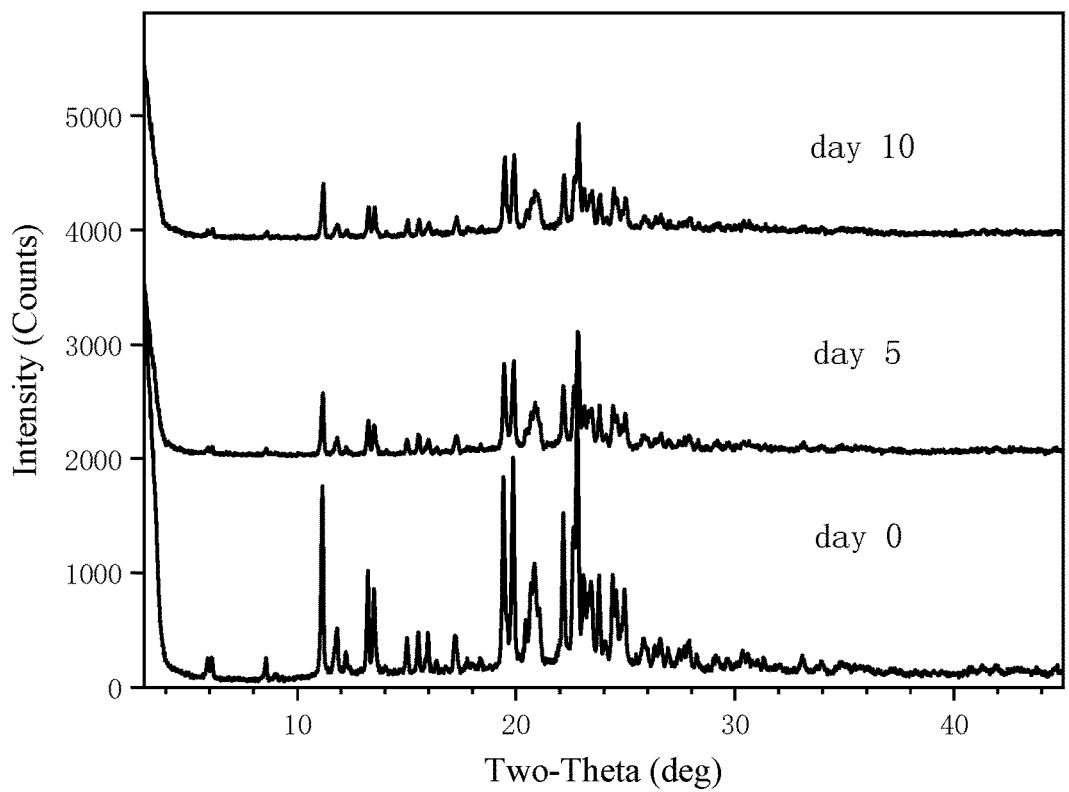
FIG. 13 shows comparison of XRPD patterns of crystal form A of the present application to study stability under high temperatures.

(2) High-temperature stability: the test sample is placed at a temperature of 60° C. for 5 days and 10 days, respectively, to test the stability of the crystal form. Samples are collected at the same point at $5^{th}$ and $10^{th}$ day to measure content by HPLC peak area normalization method. The results are shown in table 3 and FIG. 13, indicating that the crystal form A has significantly improved high-temperature stability as compared to amorphous bulk pharmaceutical chemical.

Figure 14:
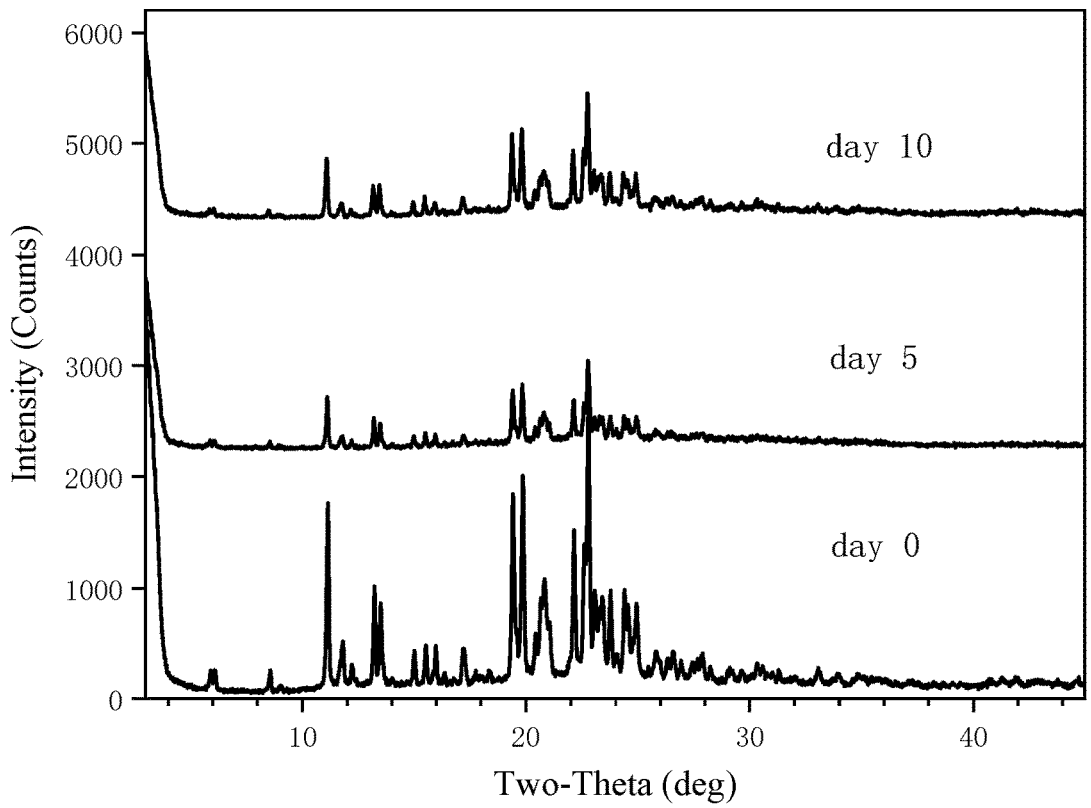
FIG. 14 shows comparison of XRPD patterns of crystal form A of the present application to study stability under high humidity.

(3) High-humidity stability: the test sample is placed in an environment having a humidity of 75% RH and a temperature of 40° C. for 5 days and 10 days, respectively, to test the stability of the crystal form. Samples are collected at the same point at $5^{th}$ and $10^{th}$ day to measure content by HPLC peak area normalization method. The results are shown in table 3 and FIG. 14, indicating that the crystal form A has significantly improved high-humidity stability as compared to amorphous bulk pharmaceutical chemical.

TABLE 3

Stability of crystal form A and amorphous bulk pharmaceutical chemical

| Experimental items | Time (day) | Purity (%) of crystal form A | Purity (%) of amorphous bulk pharmaceutical chemical |
|---|---|---|---|
| Light stability | 5 | 91.78 | 72.54 |
|  | 10 | 89.07 | 71.99 |
| High-temperature stability | 5 | 98.64 | 61.62 |
|  | 10 | 98.72 | 58.98 |
| High-humidity stability | 5 | 98.52 | 81.63 |
|  | 10 | 98.56 | 79.78 |

In summary, the crystal form A of N,N'-(10,17-dioxo-3,6,21,24-tetraoxa-9,11,16,18-tetraazahexacosane-1,26-diyl) bis(4-(6,8-dichloro-2-methyl-1,2,3,4-tetrahydroisoquinoline-4-yl) benzene sulfonamide provided in the present application has good light stability, high temperature stability, and high-humidity stability. Apparently, the aforementioned embodiments are merely examples illustrated for clearly describing the present application, rather than limiting the implementation ways thereof. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present application.

What is claimed is:

1. A crystal form A of N,N'-(10,17-dioxo-3,6,21,24-tetraoxa-9,11,16,18-tetraazahexacosane-1,26-diyl) bis(4-(6,8-dichloro-2-methyl-1,2,3,4-tetrahydroisoquinoline-4-yl) benzene sulfonamide of formula (I), wherein the X-ray powder diffraction thereof using Cu-Kα radiation has characteristic peaks at 2θ diffraction angles of 11.1±0.2°, 19.4±0.2°, 19.9±0.2° and 22.8±0.2°,

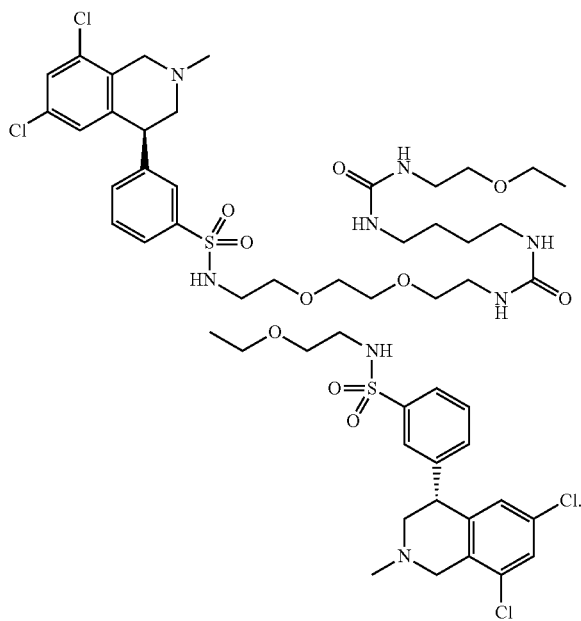

(I)

2. The crystal form A of claim 1, wherein the X-ray powder diffraction thereof using Cu-Kα radiation has further characteristic peaks at 2θ diffraction angles of 8.6±0.2°, 13.2±0.2°, 13.5±0.2°, 22.1±0.2°, and 23.8±0.2°.

3. The crystal form A of claim 2, wherein the X-ray powder diffraction thereof using Cu-Kα radiation has further characteristic peaks at 2θ diffraction angles of 20.8±0.2°, 23.1±0.2°, 23.4±0.2°, 24.4±0.2°, and 24.9±0.2°.

4. The crystal form A of claim 3, wherein the X-ray powder diffraction thereof using Cu-Kα radiation has further characteristic peaks at 2θ diffraction angles of 5.9±0.2°, 6.1±0.2°, 11.8±0.2°, 15.0±0.2°, 15.5±0.2°, 16.0±0.2°, and 17.2±0.2°.

5. The crystal form A of claim 1, wherein the crystal form A has following characteristic peaks in X-ray powder diffraction pattern:

| No. of Peaks | 2θ (°) | Relative intensity (%) |
| --- | --- | --- |
| 1 | 8.587 | 8.2 |
| 2 | 11.14 | 69.3 |
| 3 | 11.816 | 16.8 |
| 4 | 13.219 | 37.8 |
| 5 | 13.498 | 31.1 |
| 6 | 15.013 | 12.7 |
| 7 | 15.532 | 14.7 |
| 8 | 15.973 | 14.3 |
| 9 | 17.209 | 12.9 |
| 10 | 19.426 | 69.2 |
| 11 | 19.864 | 75.8 |
| 12 | 20.841 | 35.8 |
| 13 | 22.139 | 50.5 |
| 14 | 22.776 | 100 |
| 15 | 23.773 | 27.4. |

6. The crystal form A of claim 1, wherein the crystal form A has following characteristic peaks in X-ray powder diffraction pattern:

| No. of Peaks | 2θ (°) | Relative intensity (%) |
| --- | --- | --- |
| 1 | 5.913 | 7.3 |
| 2 | 6.098 | 7.6 |
| 3 | 8.587 | 8.2 |
| 4 | 11.14 | 69.3 |
| 5 | 11.816 | 16.8 |
| 6 | 13.219 | 37.8 |
| 7 | 13.498 | 31.1 |
| 8 | 15.013 | 12.7 |
| 9 | 15.532 | 14.7 |
| 10 | 15.973 | 14.3 |
| 11 | 17.209 | 12.9 |
| 12 | 19.426 | 69.2 |
| 13 | 19.864 | 75.8 |
| 14 | 20.442 | 14.4 |
| 15 | 20.841 | 35.8 |
| 16 | 22.139 | 50.5 |
| 17 | 22.776 | 100 |
| 18 | 23.059 | 26 |
| 19 | 23.398 | 25.2 |
| 20 | 23.773 | 27.4 |
| 21 | 24.395 | 30.3 |
| 22 | 24.934 | 26.4. |

7. The crystal form A of claim 1, wherein the crystal form A has an X-ray powder refraction pattern substantially as shown in FIG. 2.

8. The crystal form A of claim 1, wherein the crystal form A has a characteristic absorption peak in a temperature range of 140° C.-150° C. measured by differential scanning calorimetry.

9. The crystal form A of claim 1, wherein the crystal form A has a differential scanning calorimetry curve substantially as shown in FIG. 3.

10. The crystal form A of claim 1, wherein the crystal form A has a weight loss of 0.4% before a temperature of 100° C. in its thermo gravimetric analysis curve.

11. The crystal form A of claim 1, wherein the crystal form A has a thermo gravimetric analysis curve substantially as shown in FIG. 4.

12. A method for preparing the crystal form A of claim 1, comprising the following steps of:
dissolving amorphous N,N'-(10,17-dioxo-3,6,21,24-tetraoxa-9,11,16,18-tetraazahexacosane-1,26-di-yl)bis(4-(6,8-dichloro-2-methyl-1,2,3,4-tetrahydroisoquinoline-4-yl) benzene sulfonamide by adding a good solvent thereto,
performing a first cooling to room temperature, and adding a poor solvent thereto, and
performing a second cooling, followed by standing, separating out solids and drying to obtain the crystal form A.

13. The method of claim 12, wherein the second cooling is performed at a rate of 18-24° C./min, preferably at a rate of 20° C./min.

14. The method of claim 12, wherein the good solvent is an organic solvent selected from the group consisting of a lower alcohol, a lower ketone and a lower nitrile, and wherein the poor solvent is methyl tert-butyl ether.

15. The method of claim 14, wherein the lower alcohol is selected from the group consisting of methanol, ethanol, isopropanol or n-butanol, and the lower ketone is acetone; and the lower nitrile is acetonitrile.

16. The method of claim 12, wherein a volume ratio of the good solvent to the poor solvent is 1:(8-14).

17. A pharmaceutical composition, comprising the crystal form A of claim 1 and a pharmaceutically acceptable excipient.

18. A method for inhibiting NHE-mediated antiport of sodium ions and hydrogen ions in mammals or for treating a disease, comprising administering a pharmaceutically effective amount of the crystal form A of claim 1 or a pharmaceutical composition comprising the same, wherein the disease is selected from the group consisting of heart failure, chronic kidney disease, end-stage renal disease, liver disease, peroxisome proliferator-activated receptor gamma agonist-induced fluid retention, hypertension, edema, and gastrointestinal tract disorder in mammals.

19. The method of claim 18, wherein the administering is performed orally or by rectal suppository.

20. The method of claim 18, wherein the heart failure is congestive heart failure, and wherein the hypertension is associated with dietary salt intake; the edema is induced by chemotherapy, premenstrual fluid overload or preeclampsia; and the gastrointestinal tract disorders are gastrointestinal motility disorder, irritable bowel syndrome, chronic constipation, functional gastrointestinal tract disorders or Crohn's disease.

* * * * *